(12) United States Patent
Hantschel et al.

(10) Patent No.: US 7,569,905 B2
(45) Date of Patent: Aug. 4, 2009

(54) SYSTEMS AND METHODS FOR ELECTRICAL CONTACTS TO ARRAYS OF VERTICALLY ALIGNED NANORODS

(75) Inventors: Thomas Hantschel, Menlo Park, CA (US); Noble M. Johnson, Menlo Park, CA (US); Peter Kiesel, Palo Alto, CA (US); Christian G. Van De Walle, Santa Barbara, CA (US); William S. Wong, San Carlos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 386 days.

(21) Appl. No.: 11/015,663

(22) Filed: Dec. 20, 2004

(65) Prior Publication Data

US 2006/0131679 A1 Jun. 22, 2006

(51) Int. Cl.
*H01L 29/84* (2006.01)
(52) U.S. Cl. .............................. 257/475; 257/E23.021; 977/762
(58) Field of Classification Search ............ 202/9, 202/20, 222, 23, 24, 10, 11; 488/2, 618, 488/962, 551; 257/25, 415, 777, 734, 741, 257/749, 746, E29.082, E29.096, E29.143, 257/E29.327, E29.068, E23.068, E23.165, 257/E21.589, E23.021, E21.508, E23.025, 257/E3.008; 977/932, 762, 890, 753, 783, 977/742, 764, 767; 427/58; 117/87; 156/278
See application file for complete search history.

(56) References Cited

U.S. PATENT DOCUMENTS

| | | | |
|---|---|---|---|
| 6,297,063 B1 * | 10/2001 | Brown et al. .................... 438/2 |
| 6,340,822 B1 * | 1/2002 | Brown et al. .................. 257/25 |
| 6,401,526 B1 | 6/2002 | Dai et al. |
| 6,465,813 B2 * | 10/2002 | Ihm .............................. 257/183 |
| 6,864,162 B2 * | 3/2005 | Sungho ........................ 438/551 |
| 6,913,075 B1 | 7/2005 | Knowles |
| 2003/0165418 A1 | 9/2003 | Ajayan et al. |
| 2004/0112964 A1 * | 6/2004 | Empedocles et al. ......... 235/491 |
| 2005/0009224 A1 | 1/2005 | Yang et al. |
| 2005/0074911 A1 | 4/2005 | Kornilovich et al. |
| 2005/0130341 A1 | 6/2005 | Furukawa et al. |
| 2005/0233585 A1 * | 10/2005 | Lai et al. ...................... 438/678 |
| 2005/0279274 A1 * | 12/2005 | Niu et al. ......................... 117/2 |
| 2006/0006463 A1 | 1/2006 | Islam et al. |
| 2006/0068195 A1 * | 3/2006 | Majumdar et al. ........... 428/323 |

OTHER PUBLICATIONS

Park et al., "Schottky nanocontacts on ZnO nanorod arrays," Applied Physics Letters, vol. 82, No. 24, pp. 4358-4360, Jun. 16, 2003.
Liu et al., "Electrical Properties of zinc oxide nanowires and intramolecular *p-n* junctions," Applied Physics Letters, vol. 83, No. 15, pp. 3168-3170, Oct. 13, 2003.

(Continued)

*Primary Examiner*—Thomas L Dickey
*Assistant Examiner*—Fazli Erdem
(74) *Attorney, Agent, or Firm*—Oliff & Berridge, PLC

(57) ABSTRACT

Systems and methods may provide electrical contacts to an array of substantially vertically aligned nanorods. The nanorod array may be fabricated on top of a conducting layer that serves as a bottom contact to the nanorods. A top metal contact may be applied to a plurality of nanorods of the nanorod array. The contacts may allow I/V (current/voltage) characteristics of the nanorods to be measured.

13 Claims, 9 Drawing Sheets

OTHER PUBLICATIONS

Lee et al., "Field emission from well-aligned zinc oxide nanowires grown at low temperature," Applied Physics Letters, vol. 81, No. 19, pp. 3648-3650, Nov. 4, 2002.

Co-pending U.S. Appl. No. 11/015,665.
Co-pending U.S. Appl. No. 11/015,469.

* cited by examiner

SYSTEMS AND METHODS FOR ELECTRICAL CONTACTS TO ARRAYS OF VERTICALLY ALIGNED NANORODS

This invention was made with Government support under Contract number F49620-02-01-0343 awarded by the Air Force Office of Scientific Research. The Government has certain rights in this invention.

BACKGROUND

1. Field

This invention relates to structures and methods for making electrical contacts to vertically aligned nanorods and arrays thereof.

2. Description of Related Art

There is currently great interest in employing nanostructures in various devices. Nanostructures exhibit extraordinary potential for light emitters, field emitters, sensors, and the like. For example, gas sensors are a very attractive application of nanostructures, since high sensitivity can result from the relatively very large surface areas of nanostructures to create a large signal per unit of detected species.

Arrays of vertically aligned nanowires can be grown on a conducting buffer layer. Such arrays may be based on, for example, zinc oxide (ZnO) nanorods and are very attractive for gas sensors with high sensitivity. They offer exciting prospects for applications as electronic or optical electronic sensors and devices.

SUMMARY

Nanorods may be grown using several techniques, including, for example, vapor transport in the presence of metal catalysts, and metal-organic chemical vapor deposition. Dense arrays of nanorods may be fabricated on top of a conducting layer that may serve as a bottom contact to the nanorods. However, forming an electrical contact to the top of such nanorod arrays is challenging. For example, the nanorods in such an array may be of slightly unequal length. Thus, forming an electrical contact to the top of the nanorod array that simultaneously makes reliable electrical contacts to a plurality of nanorods may be difficult.

Structures and methods for forming an electrical contact layer to the top of a nanorod array are provided.

In various exemplary implementations, systems and methods for forming an electrical contact layer on the top of a nanorod array that simultaneously makes reliable electrical contacts to a plurality of nanorods are provided.

In various exemplary implementations, systems and methods for making electrical contacts to both the bottom and the top of a plurality of nanorods in a nanorod array are provided.

Systems and methods are also provided for forming a metal top contact to an array of nanorods which may be of slightly unequal length.

In various exemplary implementations, a structure may comprise an array of nanorods fabricated on top of a conducting layer that serves as a bottom contact to the array of nanorods. A top contact may be formed on the top of the nanorods to simultaneously make reliable electrical contacts to a plurality of the nanorods. A gap or channel may be created between the bottom and top contacts, such that a portion of the nanorods is exposed. The bottom and top contacts may allow I/V (current/voltage) characteristics to be measured, which may be sensitive to the presence of certain species in a gas to which the nanorods are exposed, such that the array of nanorods functions as a sensor.

This and other features and details are described in, or are apparent from, the following detailed description.

BRIEF DESCRIPTION OF THE DRAWINGS

Various exemplary details of systems and methods are described, with reference to the following figures, wherein.

DETAILED DESCRIPTION OF EXEMPLARY EMBODIMENTS

A top contact may be formed on top of an array of nanorods to simultaneously make reliable electrical contacts to a plurality of the nanorods. The nanorods may be substantially vertical to a bottom substrate, and may have different lengths.

Figure 1:
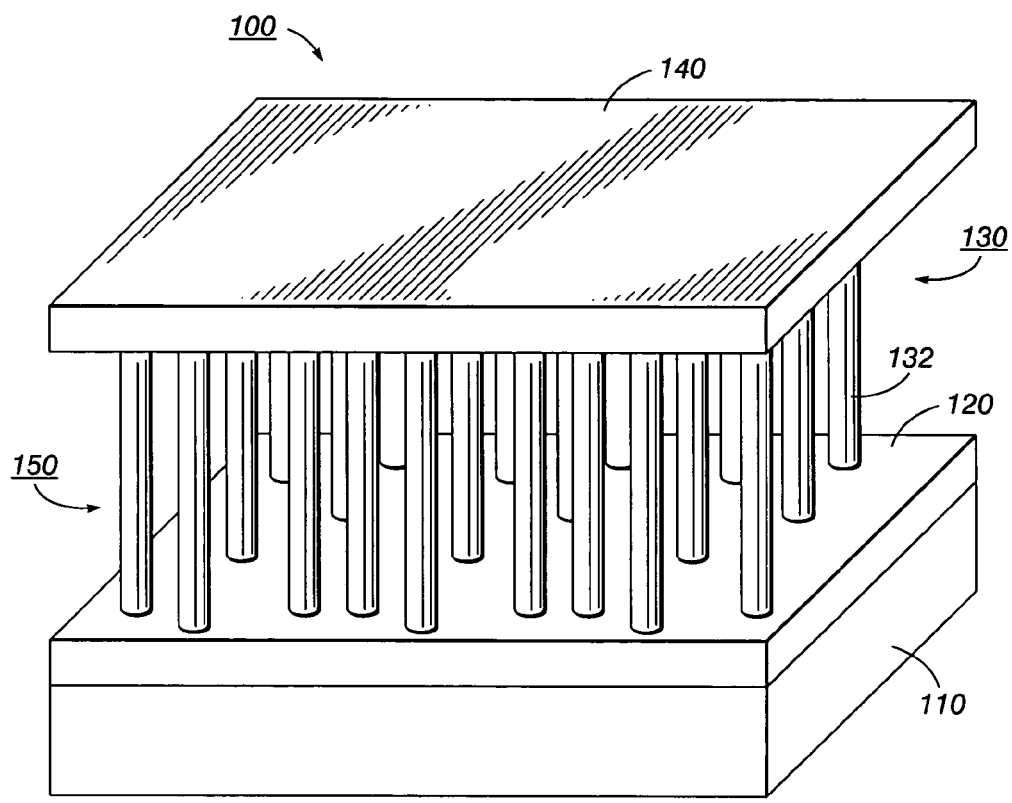
FIG. 1 illustrates an exemplary nanostructure.

FIG. 1 illustrates an exemplary nanorod device 100. As shown in FIG. 1, the nanorod device 100 may include a substrate 110, a bottom contact 120, a nanorod array 130 comprising a plurality of nanorods 132, and a top contact 140. The bottom contact 120 and the top contact 140 may be separated by a gap or channel 150.

The substrate 110 may be, for example, a sapphire, silicon, quartz, glass, metal, or organic substrate. The substrate 110 may also be other mechanically stable substrates.

The bottom contact 120 may be provided using zinc oxide (ZnO). The bottom contact 120 may also be provided using other materials, such as tin oxide, indium oxide, other binary compounds or alloys, or metals.

Each nanorod 132 in the nanorod array 130 may be substantially perpendicular to a surface of the bottom contact 120. The nanorods 132 may be grown using zinc oxide. The nanorods 132 may also be grown using silicon, carbon, metals, copper oxides, GaN, CdZnSe, Indium tin oxide (ITO), or other binary compounds or alloys. Other materials, such as tin oxide and indium oxide may also be considered for growing the nanorods 132. The top contact 140 may be a metal layer, for example, that is substantially parallel to the surface of the bottom contact 120. The top contact 140 may also be tilted relative to the surface of the bottom contact 120. In addition, the top contact 140 may also be dented, warped, or otherwise deformed. The top contact 140 may be placed in contact with a plurality of the nanorods 132 in the nanorod array 130. The nanorods 132 may include nanotubes, nanowires, nanopillars, or the like, or a combination thereof. The shape of the cross section of a nanorod may be circular, oval, hexagonal, or another shape that reflects a crystallography or intrinsic property of a material of which the nanorods are formed. The diameter of a nanorod may be the same from bottom to top across the length of the nanorod, or may change across the nanorod length. For example, a nanorod may have a pyramidal shape, or may be shaped as a truncated pyramid or a cone.

The bottom contact 120 and the top contact 140 may serve as electrodes for the nanorods 132 in the nanorod array 130.

Figure 2:
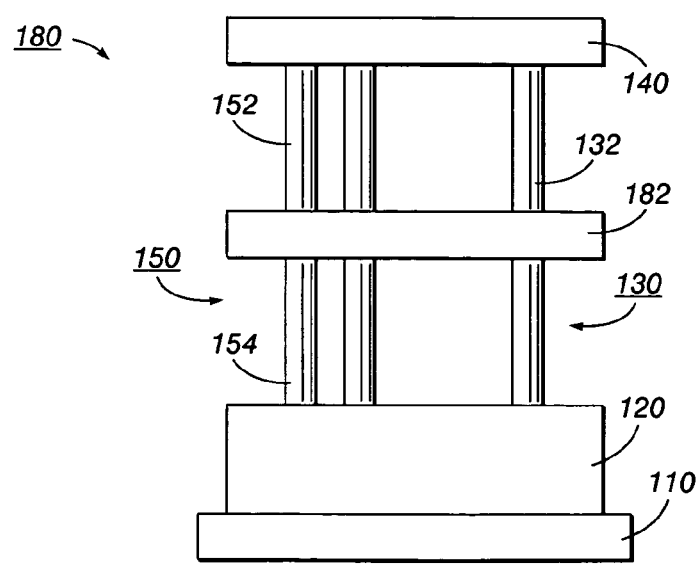
FIG. 2 illustrates another exemplary nanostructure.

FIG. 2 illustrates another exemplary nanorod device 180. The device 180 in FIG. 2 is similar to the device 100 in FIG. 1, except that the device 180 may include a third contact 182. As shown in FIG. 2, the third contact 182 may be formed between the bottom contact 120 and the top contact 140. The third contact 182 may serve as a third electrode for the nanorods 132. The third contact 182 may divide the gap 150 into an upper portion 152 and a lower portion 154, with the upper portion 152 between the top contact 140 and the third contact 182, and the lower portion 154 between the third contact 182 and the bottom contact 120.

In FIGS. 1 and 2, the gap 150 allows the nanorods 132 to be exposed to, for example, species of gas. The bottom contact 120 and the top contact 140 allow I/V (current/voltage) characteristics to be measured, which are sensitive to the presence of the species in the gas to which the nanorods 132 are exposed. For example, when a current or voltage is applied between the bottom contact 120 and the top contact 140, a variation in the current or voltage may indicate the presence of a gas species. Also, the magnitude of the variation may indicate the type or the amount of the gas species. For example, when the current changes due to both the type and the amount of the gas species, and when the type of the gas species is known, the variation of the current may indicate the amount of gas adsorbed at the nanorod surface. In such a manner, a nanorod device may be utilized as a sensitive gas sensor.

The gap 150 may also be filled with a specific material. For example, the gap 150 may be filled with a material through which the gas to be detected may easily diffuse.

Figure 3:
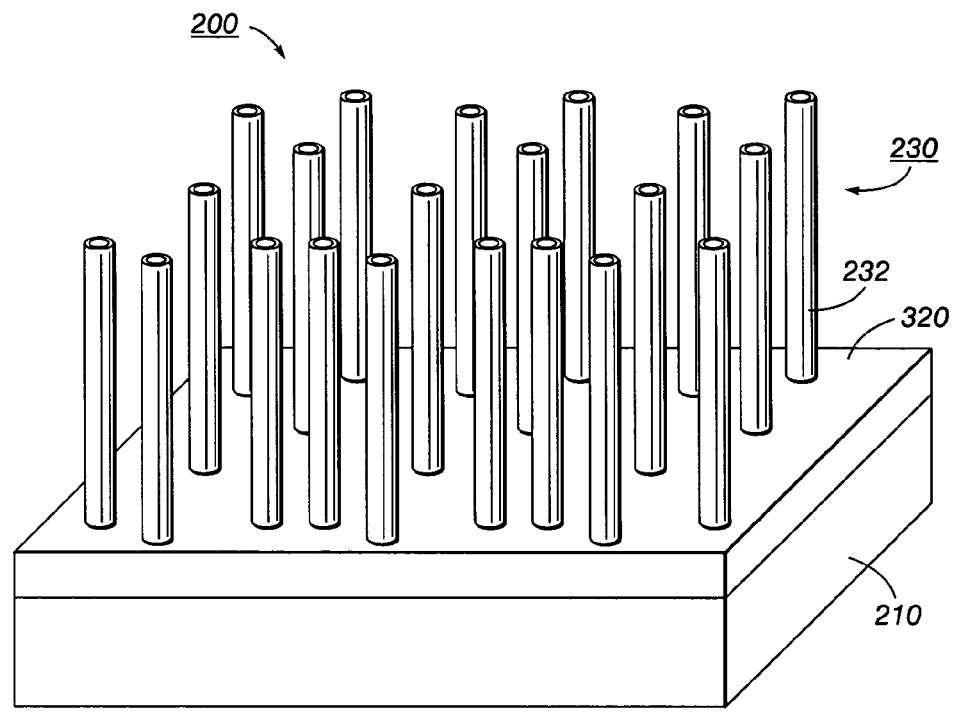
FIG. 3 illustrates an exemplary as-grown nanorod array.

FIG. 3 illustrates an exemplary as-grown nanorod array 200. As shown in FIG. 3, the nanorod array 200 may be formed, for example, by forming a zinc oxide wetting layer or buffer layer 220 on a sapphire substrate 210. The zinc oxide wetting layer 220 may be grown on the sapphire substrate 220, for example, by a metal-organic chemical vapor deposition (MOCVD) technique. The zinc oxide wetting layer 220 may also be grown on the sapphire substrate 210 using a vapor transport in the presence of metal catalysts. The nanorods may also grow on porous alumina substrates. Such a growth may be initialed on the porous surface with or without a catalyst layer for nanorod formation.

Continued growth of zinc oxide produces an array 230 containing a plurality of zinc oxide nanorods 232. The diameter of the nanorods may typically be 2 and 100 nanometers. For example, the diameter of the nanorods may be between 20 and 50 nanometers. The length of the nanorods 232 may be of several microns, such as between 1-10 microns.

The zinc oxide wetting layer 220 may comprise unintentionally doped zinc oxide, and may serve as a bottom contact to the nanorods 232. An ohmic contact may be formed, for example, by annealing indium dots on the zinc oxide wetting layer 220. The conductivity of the zinc oxide wetting layer 220 may provide a suitable bottom contact to the zinc oxide nanorods 232. For example, the zinc oxide wetting layer 220 may have a resistivity value of 1 $\Omega$/cm and carrier concentrations of about $5 \times 10^{13}/cm^2$. As discussed above, the nanorods may also be grown using silicon, carbon, metals, copper oxides, GaN, CdZnSe, Indium tin oxide (ITO), or other binary compounds or alloys. Other materials, such as tin oxide and indium oxide may also be considered for growing the nanorods. The composition of a nanorod may be constant, or it may change along the length of the nanorod. For example, the bottom portion of the nanorod could consist of one material, while the top portion consists of a different material, thus creating a heterojunction within the nanorod. In another example, the bottom portion of the nanorod may be n-type doped, while the top portion is p-type doped, thus creating a pn junction within the nanorod. Ohmic contacts to these layers may be made using a combination of the metal deposition process and transferred onto a handle wafer for access to the backside of the nanorod.

Figure 4:
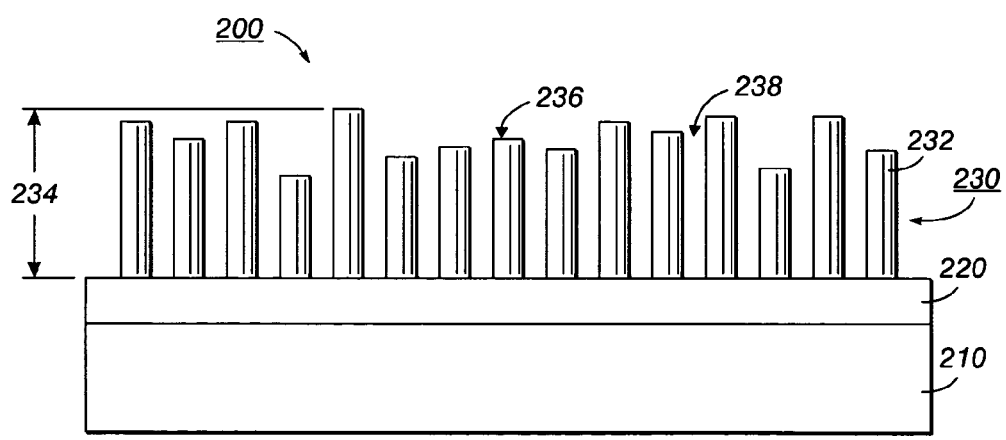
FIG. 4 illustrates a side view of the nanorod array shown in FIG. 3.
Figure 5:
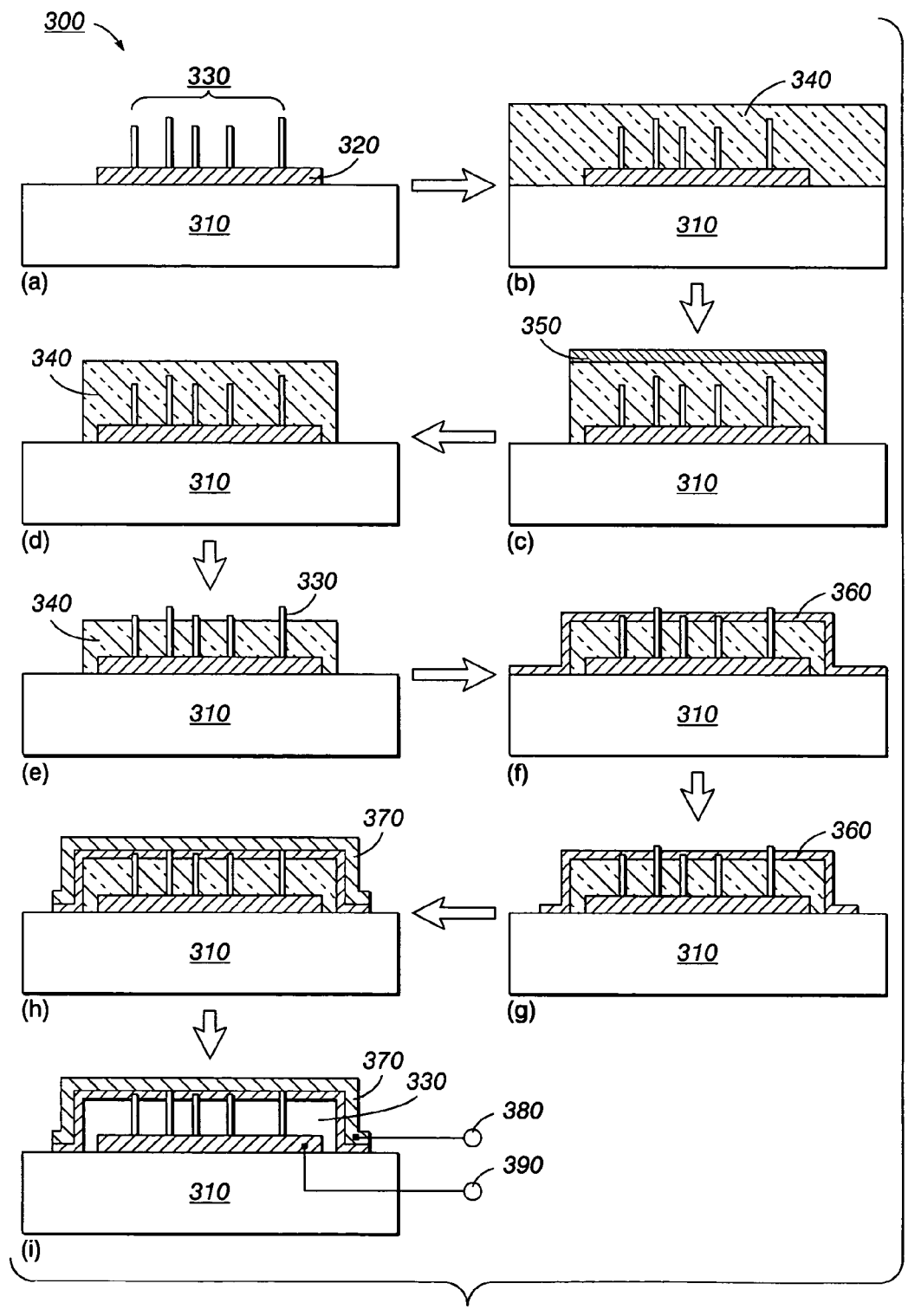
FIG. 5 outlines an exemplary process of forming a nanorod device.
Figure 6:
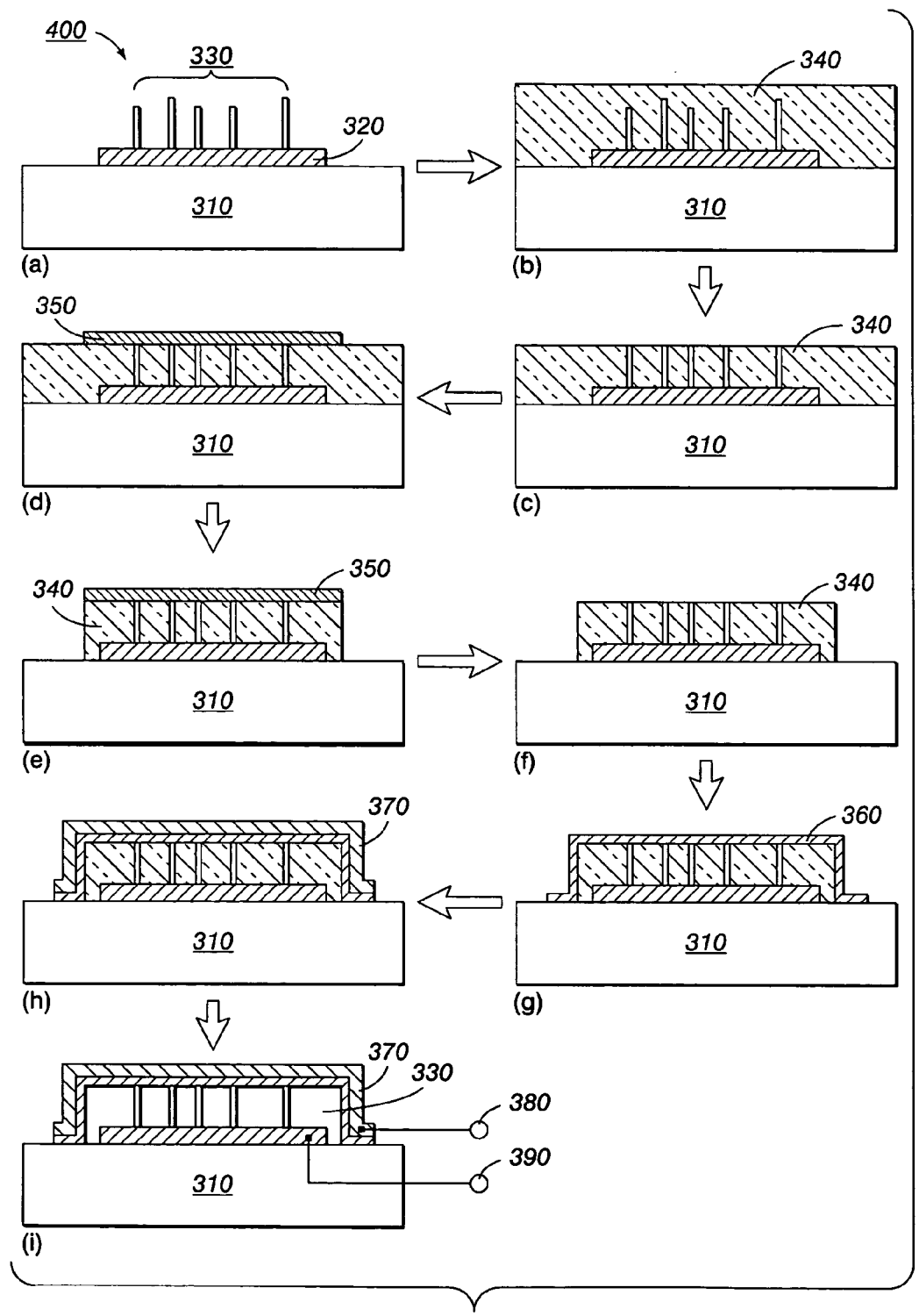
FIG. 6 outlines another exemplary process of forming a nanorod device.

FIG. 4 illustrates a side view of the nanorod array 200 shown in FIG. 3. As shown in FIG. 4, the nanorods 232 may be substantially perpendicular to a surface of the zinc oxide wetting layer 220.

A length 234 of the nanorods 232 may vary over a certain range. Thus, as shown in FIG. 4 (not to scale), tops 236 of the nanorods 232 may not be aligned in a single plane. This imposes a challenge to forming a contact, such as the top contact 140 in FIG. 1, that is capable of contacting the tops 236 of the plurality of nanorods 232 without filling spaces 238 between the nanorods 232.

FIGS. 5A-5I outline an exemplary process 300 of forming a metal top contact for a nanorod array. As shown in FIGS. 5A-5I, the exemplary process 300 of depositing a metal top contact includes using a sacrificial layer, which encapsulates the nanorods. Wet or dry etching may be used to partially expose the nanorods and allow contact with the metal. The sacrificial layer may be subsequently etched away, if necessary.

As shown in FIG. 5A, the process 300 may start by growing nanorods 330 and a bottom electrode 320 on a substrate 310. Then, as shown in FIG. 5B, a sacrificial layer 340 may be deposited to encapsulate at least some of the nanorods 330.

Next, as shown in FIG. 5C, the sacrificial layer 340 may be at least partially covered by a mask 350, and the sacrificial layer may be structured according to the pattern of the mask 350, by etching, for example, as needed. Then, as shown in FIG. 5D, the mask 350 may be removed.

Next, as shown in FIG. 5E, the sacrificial layer 340 may be partially removed, for example, to achieve a desired thickness, to expose the tops of the nanorods 330. For example, the sacrificial layer 340 may be etched by dry or wet etching to expose the nanorods 330. Then, as shown in FIG. 5F, a thin metal layer 360 may be deposited on the top of the nanorods 330 to metallize the top of the nanorods 330.

Next, as shown in FIG. 5G, the thin metal layer 360 may be structured as needed. Then, as shown in FIG. 5H, a thick metal layer 370 may be deposited.

Finally, as shown in FIG. 5I, the sacrificial layer may be removed, for example, etched away, to exposed central portions of the nanorods 330. Further, terminals 380 and 390 may be fabricated for the top electrode 370 and the bottom electrode 390, respectively. However, as discussed above in connection with FIG. 1, the sacrificial layer may remain as a material that fills the gap.

As discussed above, the top metal contact may be deposited in two steps, whereby the thin metal layer 360 is sputtered or evaporated and serves as a seed layer for a subsequent metal plating step. Electroless plating or electroplating may be used, for example. The plating of the thick metal layer 370 may provide mechanical support for the top electrode. However, the top electrode may also be fabricated using a single metallization step, for example, using sputtering, evaporation or plating techniques.

The material for fabricating the sacrificial layer 340 may be oxides, nitrides, oxy-nitrides, polymer films or metals. The sacrificial layer 340 may also be a resist layer. However, when the sacrificial layer 340 is to remain in the gap, the sacrificial layer 340 should be made from a material that is suitable for intended purposes. For example, in a device for detecting species of gas, the material should be one through which the gas to be detected may easily diffuse.

FIGS. 6A-6I outline another exemplary process 400 of forming a nanorod device. The process 400 in FIGS. 6A-6I is similar to the process 300 in FIGS. 5A-5I. Thus, like reference numbers are used for like features. However, in FIGS. 6A-6I, a chemical-mechanical polishing (CMP) technique, rather than wet or dry etching, is used to expose the nanorods. CMP may also be used to adjust the nanorods to the same length (height).

In particular, the process 400 of depositing a metal top contact includes using a sacrificial layer to encapsulate the nanorods. CMP may be used to expose the nanorods and allow contact with the metal. The sacrificial layer may be subsequently etched away, if necessary.

As shown in FIG. 6A, a nanorod array is provided. In particular, nanorods 330 and a bottom electrode 320 may be formed on a substrate 310. Next, as shown in FIG. 6B, a sacrificial layer 340 may be formed. A sacrificial layer 340 may be used to encapsulate the nanorods 330.

Then, as shown in FIG. 6C, CMP may be used to expose the tops of the nanorods 330. During this CMP process, the nanorods 330 embedded in the sacrificial layer 340 may be adjusted to the same height. The CMP step may also remove possible nanorod contaminations or insulating layers, for example, that may have developed during or after the growing process of the nanorods 330.

Next, as shown in FIG. 6D, a mask 350 may be formed for structuring the sacrificial layer 340. Then, as shown in FIG. 6E, the sacrificial layer 340 may be structured. The structuring of the sacrificial layer 340 may serve the purpose of forming the top contact in a desired fashion.

Next, as shown in FIG. 6F, the mask 350 may be removed. Then, as shown in FIGS. 5G and 5H, a thin metal layer 360 and a thick metal layer 370, respectively, may be formed.

Next, as shown in FIG. 6I, the sacrificial layer 340 may be removed, if necessary. The sacrificial layer 340 may be removed, for example, by etching or dissolving. Thereafter, terminals 390 and 380 may be formed for the bottom electrode and the thick metal layer 370, respectively. The second metal layer 370 thus may serve as the top contact for the nanorods 330.

Figure 7:
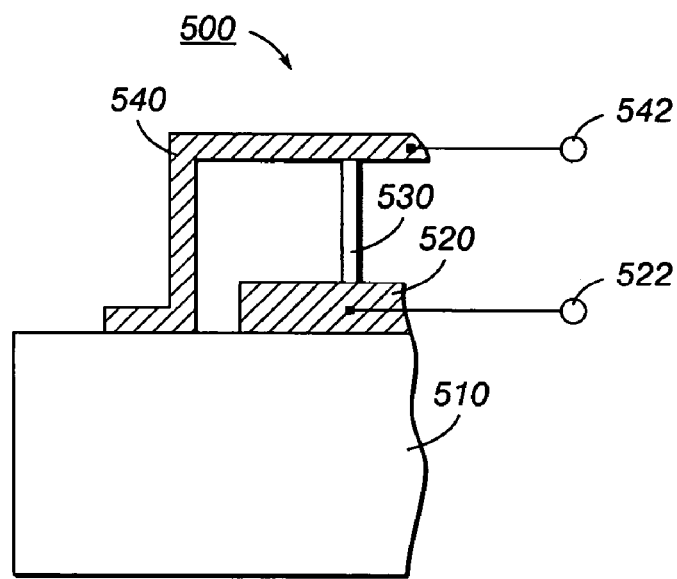
FIG. 7 illustrates another exemplary nanorod device.

FIG. 7 illustrates another exemplary nanorod device 500. As shown in FIG. 7, the nanorod device 500 is a single-nanorod device. The single-nanorod device 500 may be produced, for example, by the process shown in FIGS. 5A-5I or the process shown in FIGS. 6A-6I.

As shown in FIG. 7, the single-nanorod device 500 may include a substrate 510, a bottom contact 520, a nanorod or nanowire 530, a top contact 540, an electrode terminal 522 for the bottom contact 520, and an electrode terminal 542 for the top contact 540. The single-nanorod device 500 may serve as a passive nanorod device.

Figure 8:
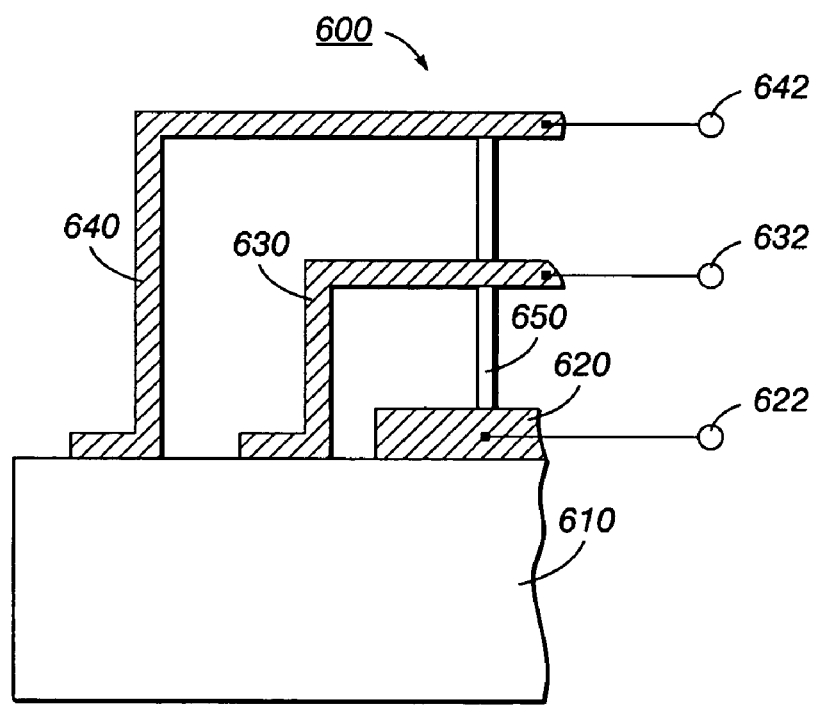
FIG. 8 illustrates another exemplary nanorod device.

FIG. 8 illustrates another exemplary nanorod device 600. As shown in FIG. 8, the nanorod device 600 may include a substrate 610, a bottom contact 620, an intermediate contact 630, a top contact 640, and a nanorod or nanowire 650. Electrode terminals 622, 632 and 642 may be provided for the bottom contact 620, the intermediate contact 630 and the top contact 640, respectively. The intermediate contact 630 and the top contact 640 may be formed, for example, by repeating the processes in FIGS. 5A-5I or the process in FIGS. 6A-6I, or by applying a combination of the processes of FIGS. 5A-5I and 6A-6I. The structures shown in FIGS. 7 and 8 may be fabricated by twice repeating the process shown in FIG. 5 or 6, or by using different materials for different layers across the nanorods. The single-nanorod device 600 may serve as an active nanorod device.

Figure 12:
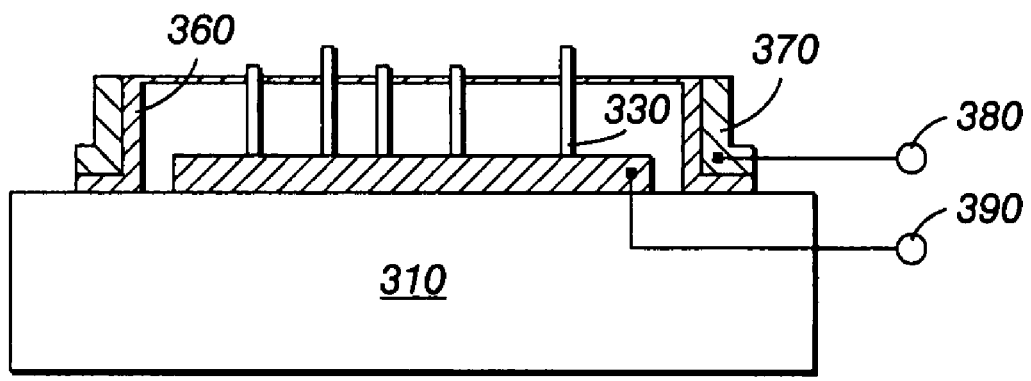
FIGS. 12 and 13 outline another exemplary process of forming a nanorod device.
Figure 13:
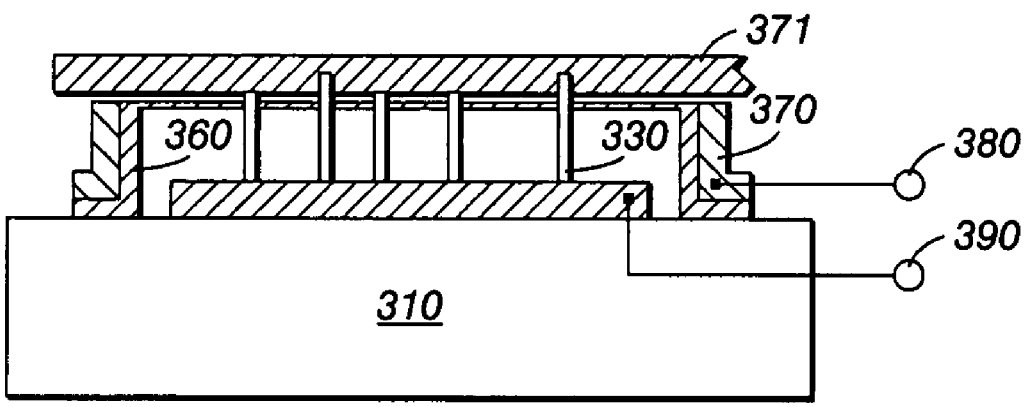

For example, after the process shown in either FIGS. 5A-5I or 6A-6I, a top thickness of the second metal layer may be removed to expose a first portion of the tops of the nanorods, as shown in FIG. 12. Next, a second sacrificial layer (not shown) may be deposited to encapsulate the first portion of the tops. Then, a top thickness of the second sacrificial layer may be removed to expose a second portion of the first portion of the tops. Finally, a second contact layer 371 may be formed on the second sacrificial layer, as shown in FIG. 13. The second contact layer may be made in electrical contact with the second portion of the first portion of the tops of the nanorods.

The nanorod device 600, having three electrodes, may be used as a transistor structure, for example. The nanorod device 600 may also be fabricated with two or more nanorods, with the intermediate contact 630 serving as the third layer 182, as discussed in connection with FIG. 2. The nanorod device 600 may also be used as an active single-nanorod device.

FIGS. 9A-9J illustrate another exemplary process 700 of forming a nanorod device. In particular, the process 700 may be used to transfer the nanorods and the sacrificial layer from the original growth substrate onto a substitute substrate, such as a handle wafer. The transfer may be desirable when the original substrate is insulating or when the original substrate needs to be more conductive.

Figure 9:
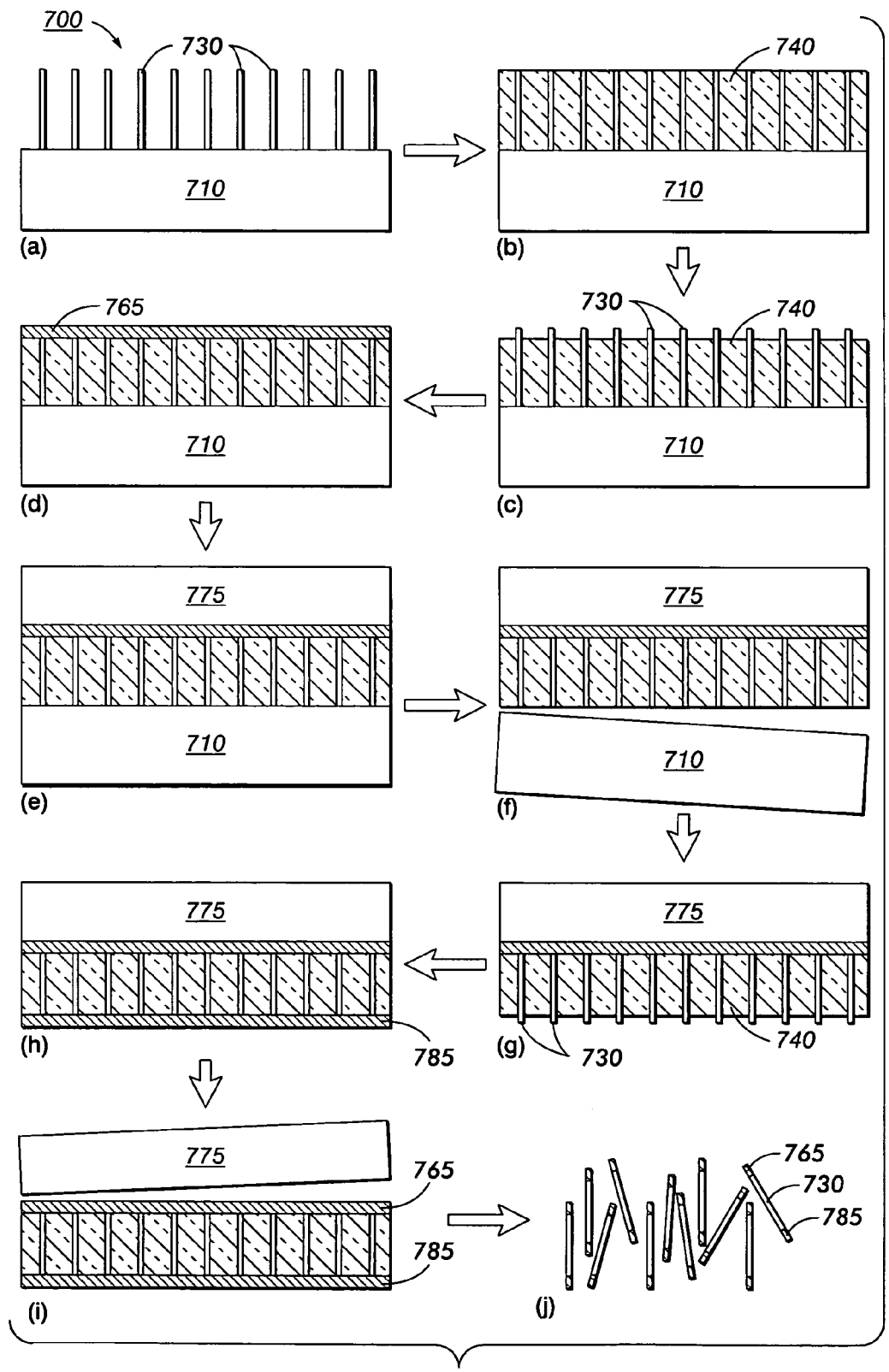
FIG. 9 outlines another exemplary process of forming a nanorod device.

As shown in FIG. 9A, the process 700 may start by growing nanorods 730 on substrate 710. Then, as shown in FIG. 9B, a sacrificial layer 740 may be deposited to encapsulate at least some of the nanorods 730. The sacrificial layer 740 may serve, for example, to mechanically reinforce the nanorods 730. The surface of the sacrificial layer 740 may be planarized by, for example, CMP.

Next, as shown in FIG. 9C, the sacrificial layer 740 may be partially removed, for example, etched, to expose the tops of at least some of the nanorods 730. The sacrificial layer 740 may be etched, for example, by dry or wet etching to expose the nanorods 730. Alternatively or additionally, CMP may be used to expose the nanorods 730. During a CMP process, the nanorods 730 embedded in the sacrificial layer 740 may be adjusted to the same length (height). The CMP may also remove possible nanorod contaminations or insulating layers.

Then, as shown in FIG. 9D, a metal layer 765 may be deposited on the tops of the nanorods 730 to metalize the tops of the nanorods 730. The metal layer 765 may serve as an electrical contact layer.

Next, as shown in FIG. 9E, a handle wafer 775 may be formed or bonded on the metal layer 765. The handle wafer 775 may be bonded using a polymeric based adhesive, such as epoxy or an ethyl cyonacrolate containing glue, or metal. The handle wafer 775 may serve, as a substitute substrate, to hold the nanorods 730 once the substrate 710 is removed, as discussed below.

Then, the substrate 710 may be removed from the nanorods 730, as shown in FIG. 9F. The nanorods 730 will not fall apart when the substrate 710 is removed because they are held by the handle wafer 775 and the sacrificial layer 740. Accordingly, the nanorods 730 are transfer from the substrate 710 to the handle wafer 775. Removal of the substrate 710 may be accomplished, for example, by ultrasonic agitation, selective chemical etching, or selective radiative irradiation, such as laser lift-off, at the interface between the substrate 710 and the nanorods 730. The handle wafer 775 may be used as a new substrate platform for the nanorods 730.

Next, as shown in FIG. 9G, the sacrificial layer 740 may be partially removed, for example, etched, to expose the bottoms of at least some of the nanorods 730. A planarization process may be performed at the bottom surface of the sacrificial layer 740 before the sacrificial layer 740 is etched.

Thereafter, as shown in FIG. 9H, a metal layer 785 may be deposited on the bottoms of the nanorods 730 to metallize the bottoms of the nanorods 730. The metal layer 785 may serve as another electrical contact layer.

Then, as shown in FIG. 9I, the handle wafer 775 may be removed. Removal of the wafer handle 775 may be accomplished, for example, by immersing in a solvent or chemical etchant, or by a laser lift-off process. Thereafter, the array of nanorods 730, having tops and bottoms metallized, may be further processed. For example, electrodes and/or terminals may be fabricated to the nanorod array. Also, other substrates, such as more conductive substrates, may be formed on the nanorod array. In addition, the sacrificial layer 740 may be removed to produce free-standing nanorods, each having its two ends metallized, as shown in FIG. 9J. The removal of the sacrificial layer may be accomplished, for example, by etching.

Alternatively, the nanorods 730 may be selectively lifted-off in a defined pattern. For example, one nanorod located at a center of the nanorod array may be selectively removed by laser lift-off. Such a lift-off may be performed when or after either or both of the substrate 710 and the wafer handle 775 is removed.

The top contact may be fabricated using a process other than those described in FIGS. 5A-5I and 6A-6I. For example, the top contact may be formed by pressing a thin metal foil against the top of the nanorod array. The thin metal foil may be a thin indium foil or a thin gallium foil.

The thin metal foil may be heated to a temperature that is close to, but below, the melting temperature of the thin metal foil. The thin metal foil may be pressed against the nanorod array such that the nanorods are pressed into the thin metal foil to the point where a plurality of the nanorods are making contact with the thin metal foil. Impurities may be added to the thin metal foil to raise its melting temperature as desired.

The thin metal foil may comprise a combination of different metals. For example, the thin metal foil may comprise a Ti/Au or Ti/Ag combination.

The thin metal foil may also be heated above its melting temperature. In such a process, the nanorod array may be turned upside down so that the nanorods, with tops down, may be inserted into the melted, liquid metal until a plurality of the nanorods make contact with the metal. The metal may then be cooled.

The thin metal foil may be a two-layer metal foil, for example, combining two different metals with different melting temperatures. A first layer may be used to provide mechanical stability, while a second layer may melt upon heating. The nanorods may be tipped, with tops down, into the liquid metal of the melted layer. The capillary adhesion of the liquid metal will help to provide contact with the nanorods. The liquid metal may then be cooled below its melting temperature. With such a process, alloyed contact for N- and P-type contacts may also be realized. Alternatively, the thin metal foil may include a metal film on a base foil. The base foil may be metallic or non-metallic. For example, the base foil may be made of a dielectric material.

The two-layer metal foil may be formed, for example, by taking the foil of one metal and evaporating a thin film of a second metal on top. The first metal may provide mechanical stability. The second metal may be tailored, for example, to have a thickness on the order of 100 nanometer. The thickness of the second metal should be much less than the length of the nanorods, but sufficient to accommodate possible variations in the length of the nanorods. The two-layer metal foil may provide a built-in p-n junction to the nanorods during the metallization process.

Figure 10:
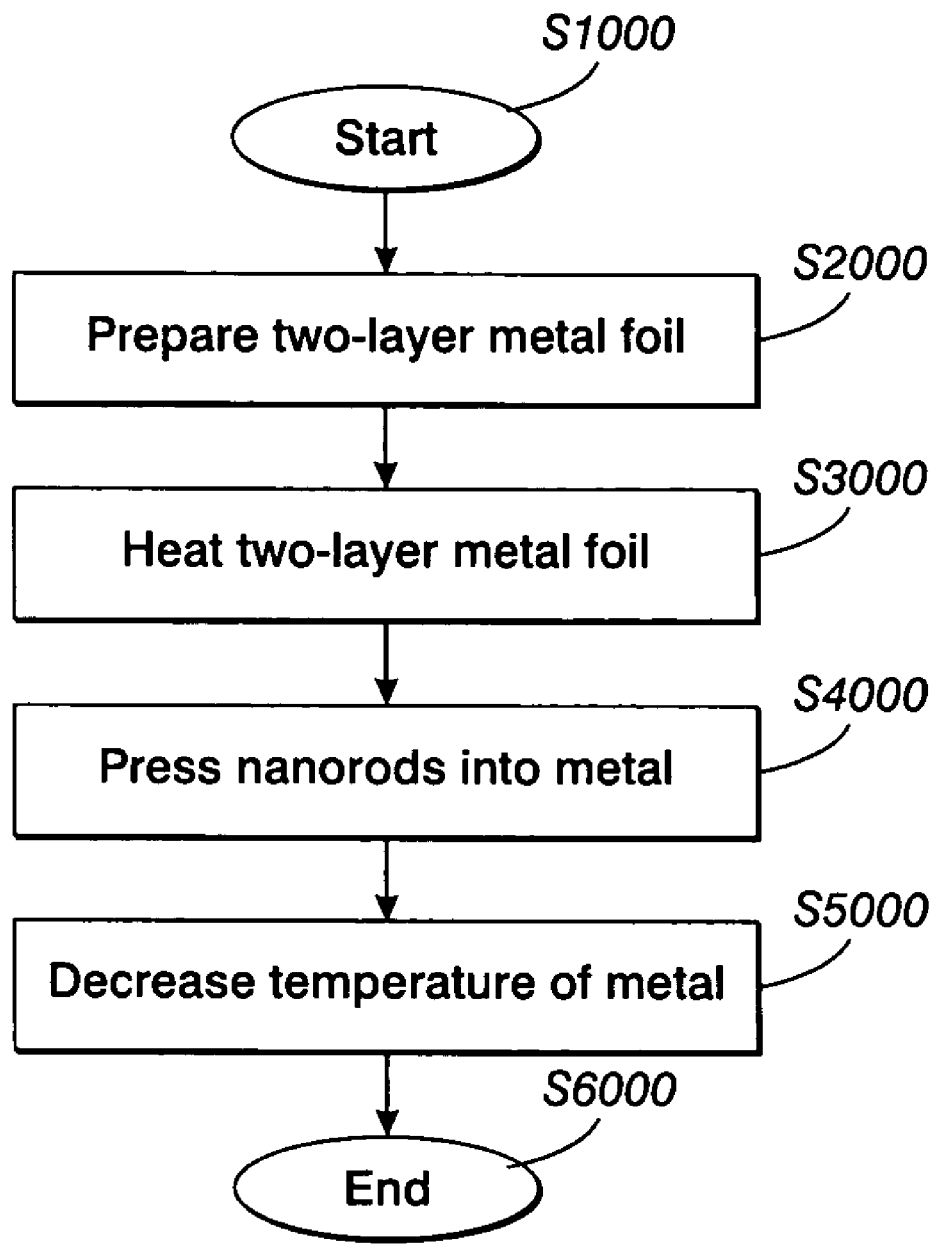
FIG. 10 illustrates a flowchart outlining an exemplary method of making a nanorod device.

FIG. 10 is a flowchart outlining an exemplary method of making a nanorod device. This method uses a two-layer metal foil, for example, as discussed above. As shown in FIG. 10, starting from step S1000, operation of the method continues to step S2000, where a two-layer metal foil is prepared. Then, in step S3000, the two-layer metal foil is heated to a temperature above the melting temperature of the second layer, but below the melting temperature of the first layer.

Next, in step S4000, the nanorods, with tops down, are pressed into the melted second layer, for example, against the first layer. Capillary adhesion of the liquid, melted metal layer may provide adequate contact between the melted metal and a plurality of nanorods. Afterwards, in step S5000, the two-layer metal foil is cooled to decrease its temperature below the melting temperature of the second layer. Thereafter, operation proceeds to step S6000, where operation of the method ends.

A nanorod device, such as those described above, may be used in various nanorod-based devices, such as light emitters, electronic devices such as transistors, or various types of sensors, such as gas sensors, pressure sensors, and temperature sensors.

Figure 11:
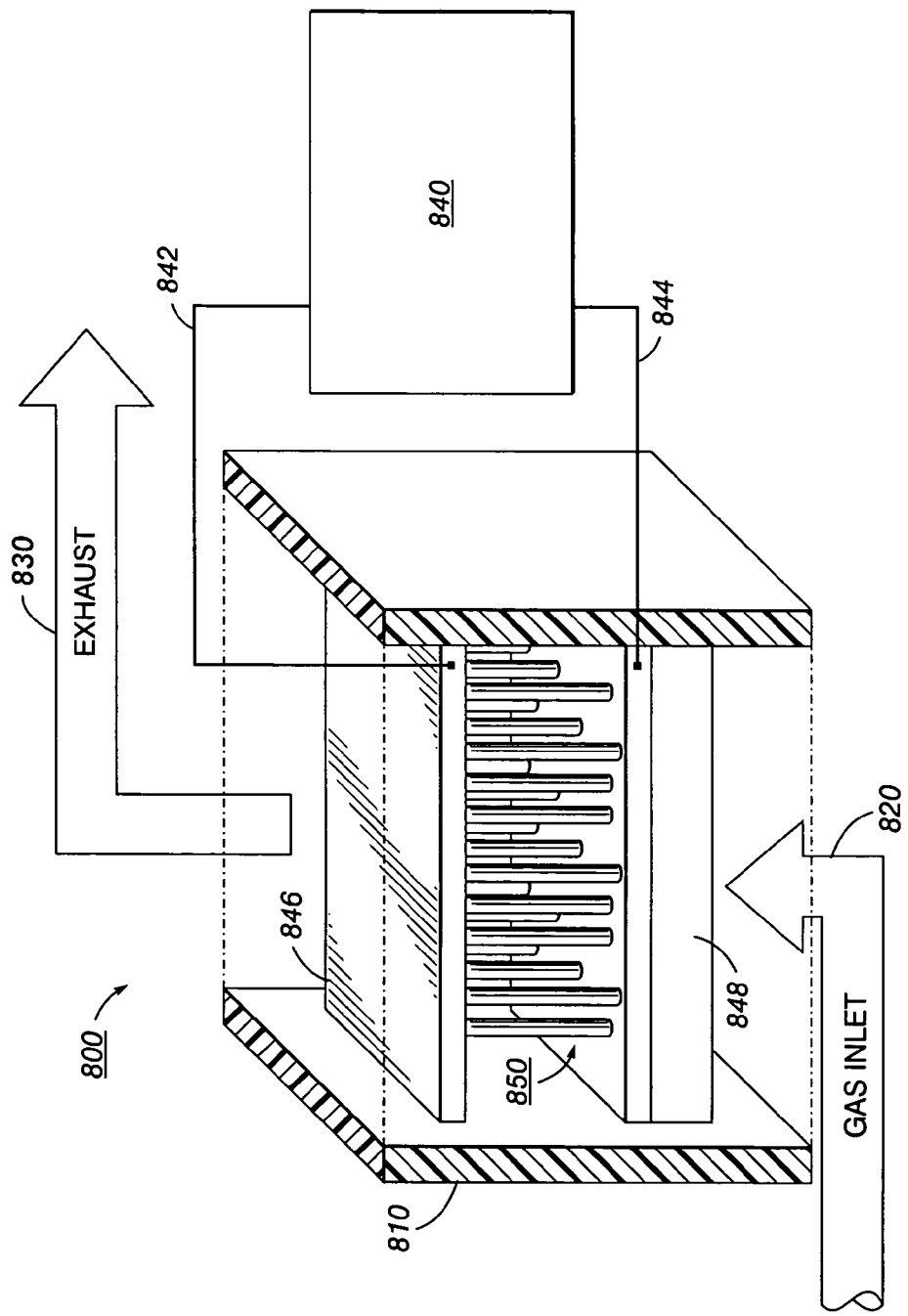
FIG. 11 illustrates an exemplary sensor system.

FIG. 11 illustrates an exemplary gas-phase chemical detection system 800 that utilizes such a nanorod device. As shown in FIG. 11, the detection system 800 may include a nanorod device 810 and an analyzer 840. The nanorod device 810 may include a first contact 846 connected to the analyzer 840 via a connection 842, and a second contact 848 connected to the analyzer 840 via a connection 844.

The nanorod device 810 may include a plurality of nanorods 850. The space between the first contact 846 and the second contact 848, and the space between the nanorods 850, may be filled with a material through which a gas to be detected may easily diffuse. The gap between the first contact 846 and the second contact 848 may also be open so as to expose the nanorods 850.

The nanorod device 810 may include, or may be connected to, a gas inlet 820. The nanorod device 810 may also include, or be connected to, an exhaust 830.

In operation, gas may be allowed via gas inlet 820 into the space between the first contact 846 and the second contact 848. The gas may exit via exhaust 830. The I/V (current/voltage) characteristics of the nanorods 850 may be influenced by the gas. Such characteristics may be analyzed by the analyzer 840, which receives information from the first and the second contacts 846 and 848 via the connections 842 and 848, respectively. The configuration shown in FIG. 11 may provide high sensitivity to the detection system 800.

The methods discussed above may be implemented in a computer program product that can be executed on a computer. The computer program product may be a computer-readable recording medium on which a control program is recorded, or it may be a transmittable carrier wave in which the control program is embodied as a data signal.

While various details have been described, these details should be viewed as illustrative, and not limiting. Various modifications, substitutes, improvements or the like may be implemented in view of the foregoing disclosure.

What is claimed is:

1. A vertically fabricated three-electrode device comprising:
   a detector having a substrate having a major surface; and a nanorod formed on the substrate, the nanorod being substantially perpendicular to the major surface of the substrate, wherein the nanorod comprises:

a middle portion;

a first end portion, the first end portion being metallized; and a second end portion, the second end portion being metallized, a part of the middle portion of the nanorod being metallized and electrically connected to a third electrode.

2. The vertically fabricated three-electrode device of claim 1, wherein the nanorod has a diameter between about 2 nanometers and about 100 nanometers.

3. The vertically fabricated three-electrode device of claim 1, wherein the nanorod has a length between about 1 micron and about 10 microns.

4. The vertically fabricated three-electrode device of claim 1, the first and second end portions of the nanorod being electrically connected to a first and second electrodes, respectively.

5. The vertically fabricated three-electrode device of claim 1, the nanorod being formed of ZnO, silicon, carbon, metal, copper oxide, GaN, CdZnSe, ITO, tin oxide, or indium oxide.

6. The vertically fabricated three-electrode device of claim 1, the nanorod being a nanotube, a nanowire or a nanopillar.

7. The vertically fabricated three-electrode device of claim 1, a shape of a cross-section of the nanorod being circular, oval, hexagonal, or another shape that reflects a crystallography or intrinsic property of a material of which the nanorod is formed.

8. The vertically fabricated three-electrode device of claim 1, the nanorod being shaped as a pyramid, a truncated pyramid a cone, or a truncated cone.

9. The vertically fabricated three-electrode device of claim 1, the nanorod having a p-n junction along a length of the nanorod.

10. The vertically fabricated three-electrode device of claim 1, the nanorod formed on a substrate, the substrate being a sapphire, silicon, quartz, glass, metal, organic or porous alumina substrate.

11. The vertically fabricated three-electrode device of claim 1, wherein the middle portion is between the first and second end portions, and the nanorod is not bundled with other nanorods.

12. The vertically fabricated three-electrode device of claim 1, the major surface being a surface on which the nanorod was originally grown.

13. A vertically fabricated three-electrode device comprising:

a transistor including a substrate having a major surface and a nanorod; and the nanorod formed on the substrate, the nanorod being substantially perpendicular to the major surface of the substrate, wherein the nanorod comprises:

a middle portion;

a first end portion, the first end portion being metallized; and a second end portion, the second end portion being metallized, a part of the middle portion of the nanorod being metallized and connected to a third electrode.

* * * * *